United States Patent [19]

Clark

[11] Patent Number: 4,836,200
[45] Date of Patent: Jun. 6, 1989

[54] OXYGEN TUBE SUPPORT STRAP

[75] Inventor: Rodney D. Clark, Egan, S. Dak.

[73] Assignee: Edward H. Lacey, Trent, S. Dak. ; a part interest

[21] Appl. No.: 161,721

[22] Filed: Feb. 29, 1988

[51] Int. Cl.⁴ .................. A61M 15/08; A62B 7/00
[52] U.S. Cl. ..................... 128/207.18; 128/204.18; 128/DIG. 26; 128/912
[58] Field of Search .............. 128/207.17, 207.18, 128/202.27, 912, 911, DIG. 15, DIG. 26, 207.11, 207.13, 204.11, 200.26, 204.18; 24/306, 442, 444; 604/174, 179

[56] References Cited

U.S. PATENT DOCUMENTS

| | | | |
|---|---|---|---|
| 3,370,818 | 2/1968 | Perr | 24/442 |
| 4,012,544 | 3/1977 | Richards | 24/306 |
| 4,018,221 | 4/1977 | Rennie | 128/207.18 |
| 4,569,348 | 2/1986 | Hasslinger | 128/DIG. 26 |
| 4,739,757 | 4/1988 | Edwards | 128/207.18 |

Primary Examiner—Edgar S. Burr
Assistant Examiner—Kimberly L. Asher

[57] ABSTRACT

A device particularly for use with a nasal cannula for holding oxygen tubes in place on a user's head free of the ears thus avoiding chafing. The device includes a head strap having loops to hold the oxygen tubes.

3 Claims, 2 Drawing Sheets

OXYGEN TUBE SUPPORT STRAP

BACKGROUND AND SUMMARY OF THE INVENTION

This invention pertains to devices adapted to provide comfort to persons required to use a constant supply of oxygen and more particularly to a device adapted to hold the oxygen tubes in a nasal cannula or the like away from the ears of the user.

Many victims of emphysema and similar lung maladies are being required to use pure oxygen on a nearly full time basis. This oxygen is normally carried from a tank through a nasal cannula to the user's nostrils. The cannula uses a tube having two branches dividing at about the chin of the user and then being draped over the ears and running to a pair of orifices directed into the user's nostrils. The orifices are held in the user's nostrils because of the position of the tubes draped over the ears. Unfortunately, for many users, the constant rubbing and pulling of the tubes on the ears causes considerable irritation and chafing.

In order to prevent such chafing, I have devised a simple, light weight and effective way of holding the tube free of the user's ears. The device has met with enthusiastic reception from users and from their doctors and nurses. The particular benefits are the light weight and simplicity of the device.

FIGURES

Figure 1:
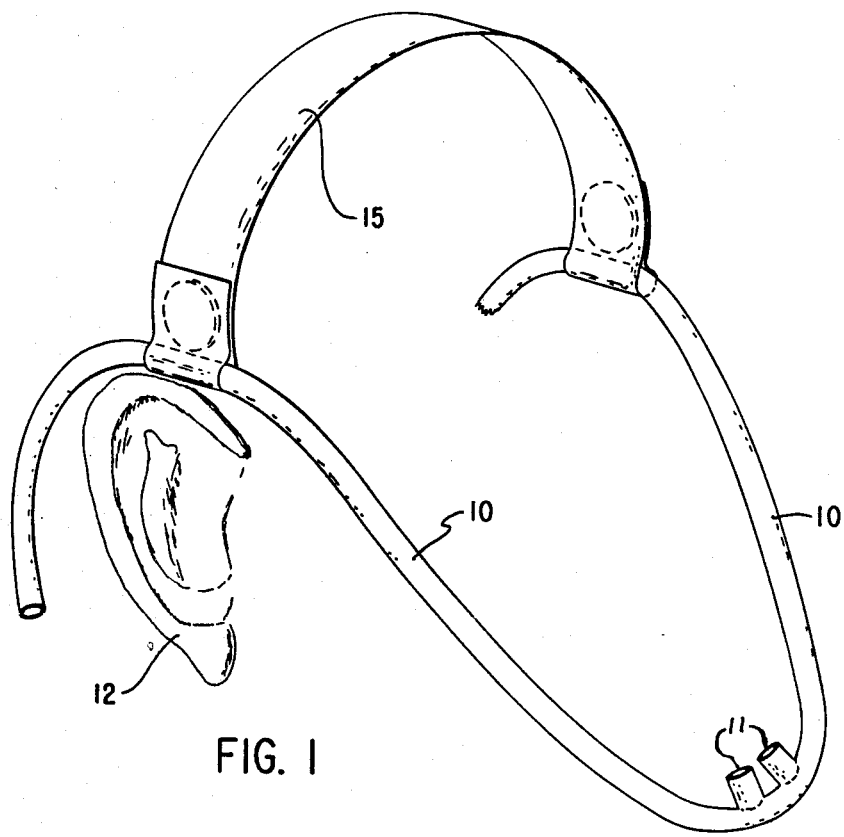
Figure 2:
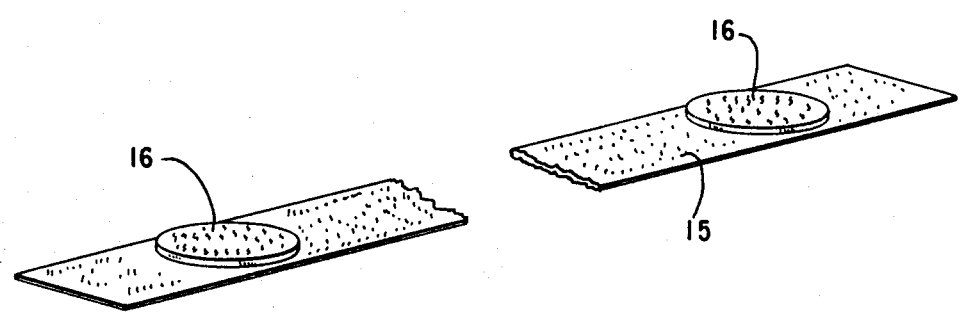
Figure 3:
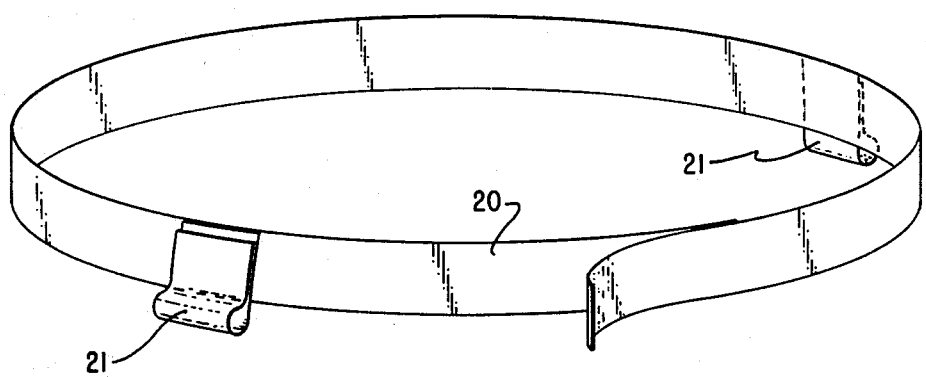

FIG. 1 is a perspective view of the device as it is used, showing the surroundings, FIG. 2 is a perspective view of the strap in a stretched out position, and FIG. 3 is a perspective view of an alternative embodiment of my invention.

DESCRIPTION

Briefly my invention comprises a strap like device extending over the head of a user of oxygen and adapted to hold the oxygen tubes of a nasal cannula free of the ears of the user.

More particularly, and referring to the drawing, my device is adapted to be used in connection with the oxygen tubes 10 which direct the oxygen from a tank, not shown, to the nostril orifices 11. Normally, the tubes 10 are draped over the ear 12 of the oxygen user, and hang onto the part of the ear nearest the user's head. The tube then normally hangs on the ear. The result is a rubbing and pulling by the tube on that part of the ear to the discomfort of the user.

By my invention I provide a strap 15 adapted to go over the top of the head of the user. This strap may be completely formed of a pressure-fastening fabric such as "Velcro", or it may carry pads of such fabric near the ends of the strap. I prefer to use an all Velcro strap for ease of manufacture.

Because the pressure-fastening fabric holds best when matched with an opposite type mating fabric, I provide small tabs 16 having both surfaces covered with the type of fabric which mates with the surface fabric on the strap 15. Thus, the tab will stay mated with and stuck to one part of the strap and released from the other. As an alternative, it will be apparent that the tip of the strap could carry one type of fabric and the rest of the strap be made from the mating type. However, I prefer to use the tabs. It may be noted that by using the tabs, their location on the strap 15 can be adjusted so that the same strap can be used on nearly any sized head.

In use, the strap should be engaged snugly about the tubes 10 not only to hold the tube but also to position the strap over the user's head. Such gripping by the strap also prevents the tubes 10 from sliding a lot when the user is turning his head.

The alternative device shown in FIG. 3 is not as desirable, in my opinion, because it requires separate fastening of the loops to the tubing and of a strap around the head. However, it will work.

The device is constructed of a strap 20 which may also use a "Velcro" fastener to hold it firmly around the user's head and forehead. Separate loop pieces 21, again fastenable with a pressure-fastening fabric are adapted to hold the oxygen tubes.

I claim as my invention:

1. In combination with a nasal cannula having tubes adapted to be draped over the ears of the user; strap means formed entirely of a pressure-fastening fabric, said strap means extending from above one ear of the user, across the top of the user's head and ending above the other ear of the user, the ends of said strap being adapted to be looped back adjacent said strap means to provide a loop above each ear of the user, means holding said tubes within the loops formed between said strap means and said ends so as to substantially prevent sliding movement of said tubes through said loops, said means including fastening tabs of double surfaced mating fabric material provided near said ends, the lengths of the portion of said strap means forming each of said loops, being substantially equal to the circumference of one of said tubes so as to hold said tubes between said strap means and said ends, to substantially prevent sliding movement of said tubes through said loops.

2. The combination of claim 1 in which said tabs are releasably fastened to said strap means whereby the location of said tabs on the strap means are adjustable.

3. The combination of claim 1 in which said pressure-fastening fabric is continuous on said strap means whereby said strap means can be tightened on said tubes in holding relationship.

* * * * *